United States Patent [19]

Takayama

[11] Patent Number: 4,949,708
[45] Date of Patent: Aug. 21, 1990

[54] HYPOTHERMIA APPARATUS
[75] Inventor: Naohiko Takayama, Kyoto, Japan
[73] Assignee: Shimadzu Corporation, Japan
[21] Appl. No.: 492,324
[22] Filed: Mar. 12, 1990

Related U.S. Application Data

[63] Continuation of Ser. No. 265,607, Nov. 1, 1988, abandoned.

[30] Foreign Application Priority Data

Nov. 6, 1987 [JP] Japan .................. 62-281491
Jan. 25, 1988 [JP] Japan .................. 63-14148

[51] Int. Cl.⁵ .............................................. A61H 1/00
[52] U.S. Cl. ................................ 128/24 A; 367/140;
128/662.03; 128/663.01
[58] Field of Search ........... 128/24 A, 662.03, 663.01,
128/24.1; 606/127, 128; 367/140

[56] References Cited

U.S. PATENT DOCUMENTS 4,207,901  6/1980  Nigam .................... 128/660
4,217,516  8/1980  Iinuma et al. ........... 310/335
4,620,546 11/1986  Aida et al. .............. 128/660
4,639,904  1/1987  Riedlinger .............. 367/140
4,771,787  9/1988  Wurster et al. ......... 128/24 A

FOREIGN PATENT DOCUMENTS 3510341 10/1986  Fed. Rep. of Germany ...... 128/328

Primary Examiner—Kyle L. Howell
Assistant Examiner—K. M. Pfaffle
Attorney, Agent, or Firm—Griffin Branigan & Butler

[57] ABSTRACT

In a hyperthermia apparatus, ultrasonic waves obtained by using an ultrasonic vibrator are focused in a living body through an acoustic lens and degassed water to form a heating region. In this case, the ultrasonic vibrator is not required to be divided, and the surface of the acoustic lens in contact with the ultrasonic vibrator and the opposite surface are formed in a concave surface, and hills and valleys spreading alternatively in the radial direction are formed on thik concave surface, and the portion between these hill and valley are formed in a plane or a curved surface. In accordance with this acoustic lens, the ultrasonic waves are focused on the heating region, and a phase difference is produced by a difference in thickness between the hill part and the valley part, and thereby no undesirable hot spots are produced behind the heating region.

3 Claims, 4 Drawing Sheets

HYPOTHERMIA APPARATUS

This is a continuation of application Ser. No. 07/265,607, filed Nov. 1, 1988, now abandoned.

BACKGROUND OF THE INVENTION

The present invention relates to a hyperthermia apparatus or thermotherapy instrument of an ultrasonic heating system, and specifically relates to an improvement in an acoustic lens disposed in front of an ultrasonic vibrator.

In curing an affected body part having abnormal cellular tissue such as cancer or other tumor, it is clinically well known that heat treatment (hyperthermia), comprising heating the affected part in a temperature range of 43° to 45° C. for a dozen to several dozen minutes is effective as a treatment.

Conventionally, the heating is applied in a manner such that an ultrasonic heating region 7a is formed in the patient's body by controlling the phase using an annular vibrator (annular array) 4a as shown in FIG. 9.

However, as shown in FIG. 9, undesirable hot spots 7b are produced behind the heating region 7a by these prior art devices.

To eliminate such undesirable hot spots, an annular vibrator 4b (FIG. 10) is further divided in the radial direction as disclosed by Japanese Patent Application Laid-Open No. 42773/1987. In this arrangement undesirable hot spots are eliminated by dividing the heating region 7a into two parts and the phases of converged ultrasonic waves are inverse to each other at the position behind the heating region 7a where the undesirable hot spots are produced.

However, this proposed vibrator divided in the radial direction has deficiencies in that the structure of the vibrator is very complicated and the control apparatus whereto a delay circuit is added becomes complicated, resulting in high cost.

SUMMARY OF THE INVENTION

An object of the present invention is to provide a hyperthermia apparatus wherein the shape of the acoustic lens used together with the vibrator is improved so as not to produce a hot spot behind the heating region, whereby a uniform heating region is obtainable.

The above-mentioned object is attainable in a manner that in the hyperthermia apparatus wherein the ultrasonic waves generated by an ultrasonic vibrator are focused on a heating region in the patient's body through the acoustic lens and degassed water, the concave surface part of the acoustic lens has hill edge lines and valley edge lines in an alternative fashion in the azimuthal direction, and the surfaces between adjacent edge lines comprise equi-interval planes or curved surfaces.

A second object of the present invention is to provide a hyperthermia apparatus, to obtain a uniform heating region, the acoustic lens is rotatable around the center together with the vibrator in the state that the portion in contact with a part to be examined is fixed.

As a means for focusing ultrasonic waves, an acoustic lens is used, and on the concave surface part thereof, oblique planes of curved surfaces are formed which continuously give portions where deviation of at least one wavelength is produced.

Also, in this case, no discontinuous portion is produced between the oblique planes.

In addition, the concave surface of the acoustic lens constituted as described above is not spherical, and therefore a uniform warming region is obtainable by rotating the lens.

Other and further details of the present invention are hereinafter described with reference to the accompanying drawings.

DESCRIPTION OF THE PREFERRED EMBODIMENTS

Figure 1:
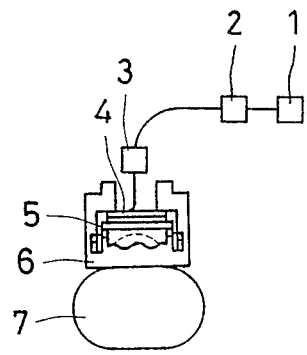
FIG. 1 is a configuration illustrating a view of a major part showing one embodiment in accordance with the present invention.

FIG. 1 illustrates hyperthermia apparatus according to one embodiment of the present invention. In this view, a high frequency wave produced by an oscillator 1 is amplified by an amplifier 2 and sent to an ultrasonic vibrator 4 through a matching circuit 3. An ultrasonic wave obtained from the ultrasonic vibrator 4 is sent to a patient's body 7 through an acoustic lens 5 and degassed water 6 in accordance with the present invention.

Figure 4:
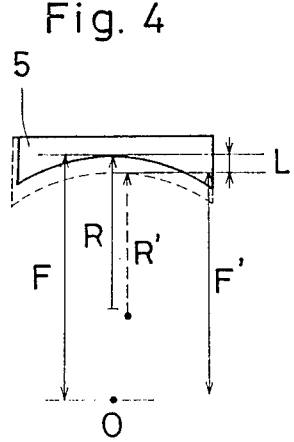
FIG. 4 is an explanatory view showing a relationship between the acoustic lens and the focal point thereof.

FIG. 4 is an explanatory view showing a relationship between the acoustic lens in accordance with the present invention and the focal point thereof.

A focal length F of an acoustic lens (curvature=R) made of aluminum is given by $F=R/(1-VW/VA)$, where VW is the velocity of sound in water (about 1530 m/S) and VA is the velocity of sound in aluminum (about R/0.76).

As shown in FIG. 4, to vary the thickness of the lens by L without varying this point of focus O, the following equations have to hold.

$$F = R'/0.76, \quad F = F' + L.$$

Consequently, if $F \gg L$, when viewed at the focal point O, the difference between a lens having a radius of R and a lens having a radius of R' is only the phase difference attending on the thickness difference L. In addition, to produce a phase difference of one wavelength, L has only to be set as follows.

$$L = \lambda/(1 - VW/VA).$$

Figure 10:
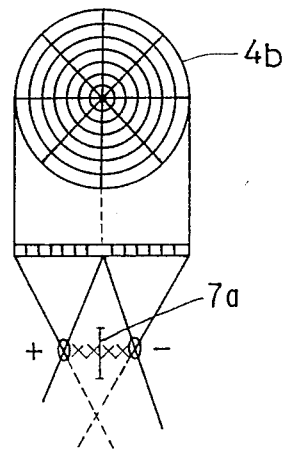
FIG. 10 is a plan view of another conventional example.

Accordingly, by using the lens having the thickness difference as described above, an acoustic field similar to the acoustic field obtained by using the vibrator as shown in FIG. 10 is obtainable.

Figure 2:
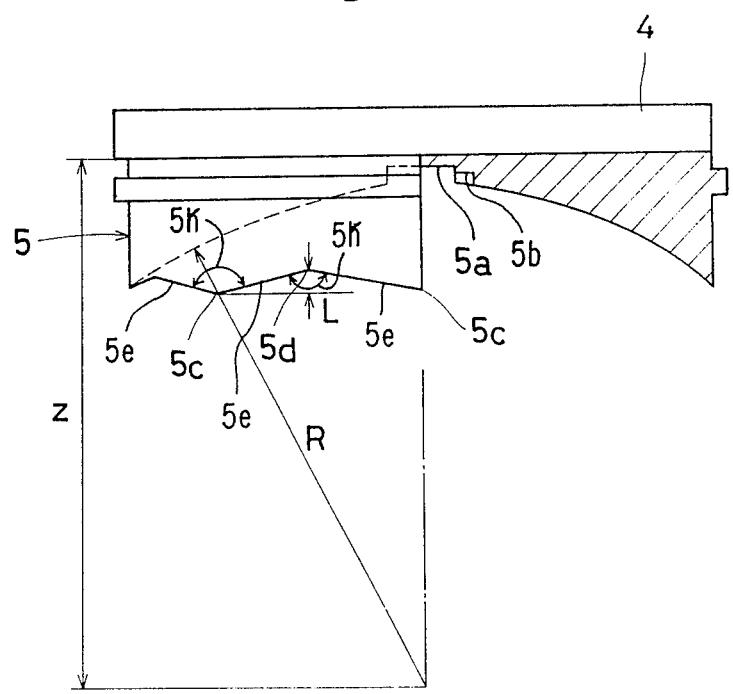
FIG. 2 is a front view showing one example of an acoustic lens in accordance with the present invention.
Figure 3:
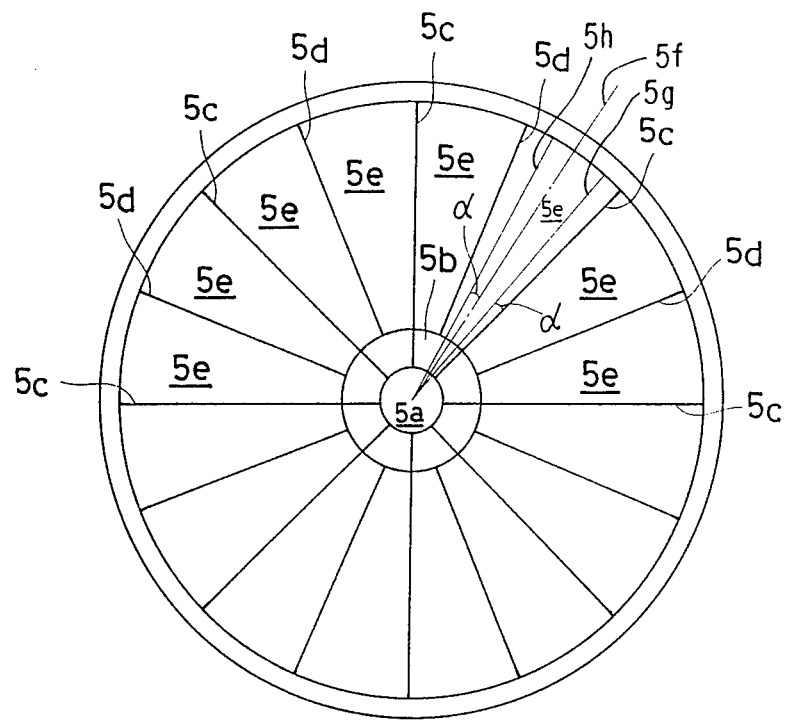
FIG. 3 is a bottom surface view or a development view of a concave surface part of the same.

FIG. 2 is a semi-cross-sectional front view showing one example of an acoustic lens in accordance with the present invention, and FIG. 3 is a bottom surface view or a development view of the concave surface part of that lens.

As shown in FIG. 2, the acoustic lens has a thickness difference of L. R is a radius of curvature, and Z is a distance between the bottom surface of the lens and the position of center of curvature.

Numeral 5a designates a center recess, and numeral 5b designates a stepped part, and these portions are required for working in fabricating the acoustic lens with metal such as aluminum.

Numerals 5c designate hill edge lines, and numerals 5d designate valley edge lines. The respective plural edge lines 5c and 5d are formed in an equi-interval fashion in the azimuthal direction, and an oblique plane part 5e is formed between two edge lines 5c and 5d. That is, a sectional plane is bounded by an adjacent pair of edge lines with the sectorial planes being equal in size.

As best illustrated in FIG. 2, the angles 5k formed between any two adjacent planes are equal and greater than 90 degrees.

In FIG. 3, a hill edge line 5c and an imaginary line 5f extending in the radial direction and bisecting an oblique plane part 5e have phases inverse to each other at focusing. Also, imaginary radial line 5g making an angle of α with the hill edge line 5c and a radial line 5h making the same angle α with the line 5f similarly have phases inverse to each other. When the whole oblique plane 5e is formed as described above, deviation of one wavelength is produced continuously in the circumferential direction to make the state of phases inverse to one another and the ultrasonic waves cancel one another.

Accordingly, by using such an acoustic lens, an acoustic field is formed wherein no undesirable hot spots are produced at the position of focus.

In addition, the material for the acoustic lens is selected from among materials having a sound velocity higher than that of water such as acrylate resin, polystyrene resin or aluminum.

Also, where the acoustic lens is fabricated with aluminum, machine work by numeric control is effective, and in this case, the work is performed by evaluating the work conditions for every angle in the circumferential direction from the reference line in the azimuthal direction, for example, with the radius of curvature R, the position of center of curvature Z and the like taken as parameters.

Figure 7:
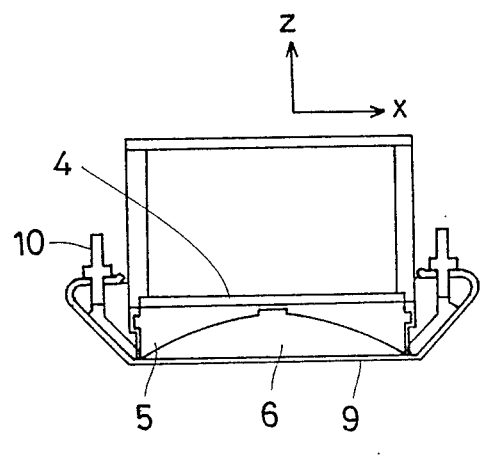
FIG. 7 is a cross-sectional view of a major part like the case of FIG. 1.

In FIG. 7 is a schematic cross-sectional view of a wave generator employing an acoustic lens 5 of the same configuration as described above. The ultrasonic wave generated by the vibrator 4 is focused by the acoustic lens 5, and is projected through the degassed water 6 and a porous wall 9 to the patient.

Numeral 10 designates an inlet for the degassed water. The degassed water 6 is passed through a circulation-cooling apparatus (not illustrated) through the inlet 10 so as to circulate and maintain the temperature of the water at a constant value.

Figure 8:
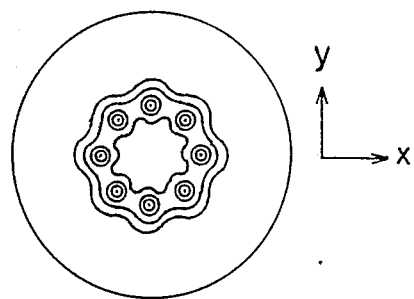
FIG. 8 is an isothermal line distribution graph by the FIG. 7 embodiment.
Figure 9:
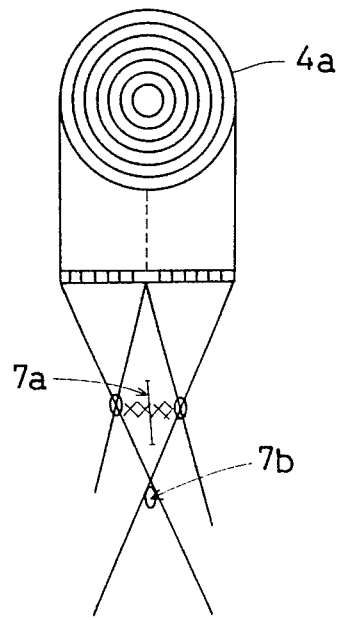
FIG. 9 is a plan view, cross-sectional view and operation explanatory view of a conventional example.

FIG. 8 illustrates the temperature distribution obtained using such an applicator as described above. This view shows isothermal lines on the cross-section at a right angle with the center axis (z direction) of the applicator. The temperature distribution spreads in a deformed circumferential shape, and particularly spot-shaped high-temperature regions are produced on a circumference in an isolated fashion, and the temperature distribution is uneven over the whole area.

Figure 5:
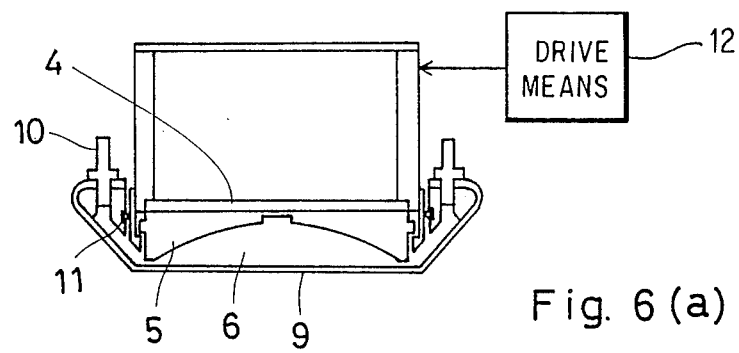
FIG. 5 is a cross-sectional view of another preferred major part.

FIG. 5 illustrates an embodiment for eliminating such unevenness of the temperature distribution. In FIG. 5, an O-ring 11 provides a water seal between the parts which, with porous wall 9, remain stationary, and the vibrator 4 and acoustic lens 5 which are rotatable relative to the porous wall. A rotational drive means 12 rotates the vibrator 4 and acoustic lens 5.

Figure 6A:
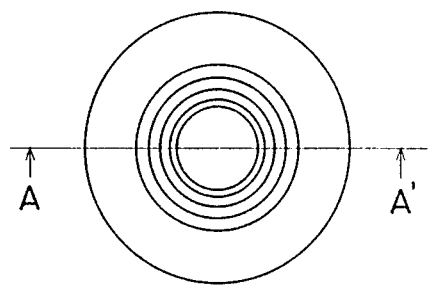
FIG. 6 are an isothermal line distribution graph by FIG. 5 embodiment and a temperature distribution graph along line A—A' in that graph.
Figure 6B:
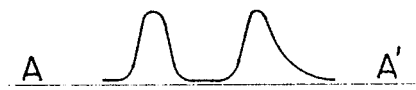

FIG. 6a is an isothermal line distribution graph illustrating the thermal distribution obtained by rotating the vibrator 4 and the acoustic lens 5 of FIG. 5 and FIG. 6b is a temperature distribution graph along line A—A' of FIG. 6a.

As illustrated, the isothermal distribution of heating region spreads in a concentric circumference fashion, and the heating region is heated uniformly, and this uniform distribution is effective when applied to the heating treatment.

In addition, the direction of rotating the acoustic lens together with the vibrator is not limited to one direction, and a method of reverse rotation on a one revolution basis may be applied. Also, the means of rotation is not illustrated particularly, but is used by selecting from among various publicly known mechanisms.

In accordance with the present invention, the vibrator is not required to be divided, and therefore the vibrator and the drive circuit thereof are simplified, and by using this acoustic lens, an ultrasonic heating apparatus can be provided at a low price wherein no undesirable hot spots are produced and the heating region is obtained in uniform warming.

What is claimed is:

1. In a hyperthermia apparatus having an ultrasonic vibrator for producing an ultrasonic wave and a rotatable acoustic lens for directing said ultrasonic wave through degassed water and focusing it in a patient's body to thereby heat a portion of said body, the improvement wherein said acoustic lens comprises:

a circular lens body, one side of said body being concave and comprising a plurality of contiguous equal surface segments symmetrically arranged about the center of the lens body, each of said surface segments being bounded at one side by a hill edge line and at the other side by a valley edge line, each said hill edge line and each said valley edge line being at the apex of an angle formed by said intersecting contiguous surface segments, said hill edge lines and said valley edge lines extending azimuthally relative to the center of said circular lens body, such that the thickness of said lens body at a given position along any of said hill edge lines is thicker than the thickness of said lens body at a corresponding position along any of said valley lines by a factor $\lambda/(1-VW/VA)$ where $\lambda$ is the wave length of said ultrasonic wave, $VW$ is the velocity of sound in water, and $VA$ is the velocity of sound in said lens body;

the angle formed between any two of said intersecting contiguous surface segments being greater than 90 degrees.

2. In a hyperthermia apparatus having an ultrasonic vibrator for producing an ultrasonic wave and a rotatable acoustic lens for directing said ultrasonic wave through degassed water and focusing it in a patient's body to thereby heat a portion of said body, the improvement wherein said acoustic lens comprises:

a circular lens body, one side of said lens body being concave and comprising a plurality of contiguous equal surface segments symmetrically arranged about the center of the lens body, a second, opposing side of said lens body being flat;

each of said surface segments being bounded at one side by a hill edge line and at the other side by a valley edge line, each said hill edge line and each said valley edge line being at the apex of an angle formed by said intersecting contiguous surface segments, said hill edge lines and said valley edge lines extending azimuthally relative to the center of said circular lens body, such that the thickness of said lens body at a given position along any of said hill edge lines is thicker than the thickness of said lens body at a corresponding position along any of said valley lines by a factor $\lambda/(1 - VW/VA)$ where $\lambda$ is the wave length of said ultrasonic wave, VW is the velocity of sound in water, and VA is the velocity of sound in said lens body;

the angle formed between any two of said intersecting contiguous surface segments being greater than 90 degrees.

3. In a hyperthermia apparatus having an ultrasonic vibrator for producing an ultrasonic wave and a rotatable acoustic lens for directing said ultrasonic wave through degassed water and focusing it in a patient's body to thereby heat a portion of said body, the improvement wherein said acoustic lens comprises:

a circular lens body, one side of said lens body being concave and comprising a plurality of contiguous equal surface segments symmetrically arranged about the center of the lens body, a second, opposing side of said lens body being flat;

each of said surface segments being bounded at one side by a hill edge line and at the other side by a valley edge line, each said hill edge line and each said valley edge line being at the apex of an angle formed by said intersecting contiguous surface segments, said hill edge lines and said valley edge lines extending azimuthally relative to the center of said circular lens body, such that the thickness of said lens body at a given position along any of said hill edge lines is thicker than the thickness of said lens body at a corresponding position along any of said valley lines by a factor $\lambda/(1 - VW/VA)$ where $\lambda$ is the wave length of said ultrasonic wave, VW is the velocity of sound in water, and VA is the velocity of sound in said lens body;

the angle formed between any two of said intersecting contiguous surface segments being greater than 90 degrees;

each said surface segment comprising an oblique plane and the thickness of said lens body varying such that ultrasonic waves passing through the oblique plane at a point midway between the hill edge line and a the valley edge line and ultrasonic waves passing through the lens body at one of said hill edge lines arrive at the focal point of the lens body with inverse phases and cancel each other.

* * * * *